(12) United States Patent
Pachys (10) Patent No.: US 8,391,550 B2
(45) Date of Patent: Mar. 5, 2013

(54) METHOD AND SYSTEM FOR DIAGNOSING AND TREATING A PEST INFESTED BODY

(76) Inventor: Freddy Pachys, Doar Na Shimshon (IL)

( * ) Notice: Subject to any disclaimer, the term of this patent is extended or adjusted under 35 U.S.C. 154(b) by 929 days.

(21) Appl. No.: 12/515,750

(22) PCT Filed: Nov. 27, 2007

(86) PCT No.: PCT/IL2007/001460
§ 371 (c)(1),
(2), (4) Date: Jun. 16, 2009

(87) PCT Pub. No.: WO2008/065650
PCT Pub. Date: Jun. 5, 2008

(65) Prior Publication Data
US 2010/0054543 A1    Mar. 4, 2010

(30) Foreign Application Priority Data
Nov. 27, 2006    (IL) .......................................... 179639

(51) Int. Cl.
*G06K 9/00* (2006.01)
(52) U.S. Cl. .......................... 382/103; 382/110; 382/173
(58) Field of Classification Search .................... None
See application file for complete search history.

(56) References Cited

U.S. PATENT DOCUMENTS

| | | | | |
|---|---|---|---|---|
| 2,737,594 A * | 3/1956 | Katz et al. ........................ | 378/58 |
| 4,283,629 A | 8/1981 | Habermehl et al. | |
| 4,943,987 A * | 7/1990 | Asahina et al. .............. | 378/98.5 |
| 5,023,805 A * | 6/1991 | Aune et al. ...................... | 702/38 |
| 5,253,302 A * | 10/1993 | Massen ........................... | 382/110 |
| 5,546,475 A * | 8/1996 | Bolle et al. ..................... | 382/190 |
| 5,771,169 A * | 6/1998 | Wendte .............................. | 702/5 |
| 5,852,646 A * | 12/1998 | Klotz et al. ......................... | 378/8 |
| 5,864,984 A * | 2/1999 | McNertney ................ | 47/58.1 R |
| 6,002,958 A * | 12/1999 | Godik ............................ | 600/407 |
| 6,081,606 A * | 6/2000 | Hansen et al. ................ | 382/107 |
| 6,256,368 B1 * | 7/2001 | Hsieh et al. ........................ | 378/8 |
| 6,359,597 B2 | 3/2002 | Haj-Yousef | |
| 6,445,409 B1 * | 9/2002 | Ito et al. ........................ | 348/155 |
| 6,505,146 B1 * | 1/2003 | Blackmer ..................... | 702/189 |

(Continued)

OTHER PUBLICATIONS

Toews et al., Publication from Journal of Economic Entomology, "Imaging and Automated Detection of *Sitophilus oryzae* (Coleoptera: Curculionidae) Pupae in Hard Red Winter Wheat", Apr. 2006, pp. 583-592.*

(Continued)

*Primary Examiner* — Manav Seth
(74) *Attorney, Agent, or Firm* — Roach Brown McCarthy & Gruber, P.C.; Kevin D. McCarthy (57) ABSTRACT

According to one aspect, the invention provides a method for detecting pest infestation within a body. The method comprises the steps of a) providing an imaging system comprising at least a radiation source, a detector, a processing station and a display monitor; b) positioning at least a section of the body between the radiation source and the detector; c) acquiring a first image of said section of said body; d) acquiring at least one second image of the section of the body; e) removing the common portion of the images by subtracting the first image from the second image, thereby resulting in a digitally subtracted image; and f) observing determining from the digitally subtracted image and determining whether at least one pest is present within the body. Pest infestation may be detected without physical contact with the tree.

15 Claims, 7 Drawing Sheets

U.S. PATENT DOCUMENTS

| | | | |
|---|---|---|---|
| 6,628,805 B1* | 9/2003 | Hansen et al. | 382/107 |
| 6,940,945 B2* | 9/2005 | Maschke | 378/98.12 |
| 7,123,750 B2* | 10/2006 | Lu et al. | 382/110 |
| 7,239,720 B2* | 7/2007 | Shima | 382/107 |
| 7,367,155 B2* | 5/2008 | Kotyk et al. | 47/14 |
| 7,445,377 B2* | 11/2008 | Lee et al. | 374/5 |
| 7,496,228 B2* | 2/2009 | Landwehr et al. | 382/170 |
| 7,715,013 B2* | 5/2010 | Glaser et al. | 356/448 |
| 7,724,871 B2* | 5/2010 | Boyden et al. | 378/87 |
| 7,773,722 B2* | 8/2010 | Boyden et al. | 378/44 |
| 7,902,256 B2* | 3/2011 | Ping | 514/549 |
| 7,916,951 B2* | 3/2011 | Landwehr et al. | 382/224 |
| 8,139,858 B1* | 3/2012 | Landwehr et al. | 382/170 |
| 2001/0007593 A1* | 7/2001 | Oosawa | 382/132 |
| 2001/0046310 A1* | 11/2001 | Shima | 382/107 |
| 2002/0092990 A1* | 7/2002 | Toomey | 250/341.1 |
| 2003/0142852 A1* | 7/2003 | Lu et al. | 382/110 |
| 2004/0071265 A1* | 4/2004 | Maschke | 378/98.11 |
| 2004/0190586 A1* | 9/2004 | Lee et al. | 374/5 |
| 2005/0017186 A1* | 1/2005 | Davies | 250/370.08 |
| 2005/0025357 A1* | 2/2005 | Landwehr et al. | 382/170 |
| 2006/0112628 A1* | 6/2006 | Kotyk et al. | 47/58.1 SE |
| 2007/0065857 A1* | 3/2007 | Glaser et al. | 435/6 |
| 2009/0153659 A1* | 6/2009 | Landwehr et al. | 348/135 |

OTHER PUBLICATIONS

S. Johnson et al. (2004) Ecological Entomology; vol. 29, No. 1, pp. 117-122.

S. Johnson et al. (2007) Agricultural and Forest Entomology; vol. 9, No. 1, pp. 39-46.

R. Fisher et al. (1940) Annals of Applied Biology; vol. 27, No. 1, pp. 92-100.

P. Cruvinel et al. (2003) Revista Arvore; vol. 27, No. 5, pp. 747-752.

* cited by examiner

METHOD AND SYSTEM FOR DIAGNOSING AND TREATING A PEST INFESTED BODY

REFERENCE TO CO-PENDING APPLICATIONS

This application claims priority as a 371 of international of PCT/IL2007/001460, filed on Nov. 27, 2007; which claims priority from Israeli patent application no. 179639, filed on Nov. 27, 2006.

FIELD OF THE INVENTION

The present invention relates in general to the field of pest infestation. In particular, the present invention relates to a method and system for determining whether a body is infested with pests.

BACKGROUND OF THE INVENTION

Pest infestation of any object or body, such as in wood construction, or living plants, plant products or trees can be damaging to many areas of society. In the field of agriculture, pest infestation reduces the quality and quantity of harvestable crops. This causes an economic loss to the harvester, which in turn raises the price of these crops for the consumer. Furthermore, pests carry and spread diseases which are harmful to both the environment and to humans. Shipments of goods, particularly food products, are typically entirely discarded if even only one box is found to be carrying pests, which causes tremendous financial loss.

One example of a body in which pests particularly enjoy infesting is the tree. Trees play a vital role in many aspects of the subsistence of the world and its inhabitants, in such areas as ecology and agriculture, as well as in providing energy and raw material for such things as paper and lumber. One example of a tree species which is considered to be important to both natural landscape and for cultivation of its fruit is the *Phoenix dactylifera* L., or, the date palm.

Since antiquity, date palm distribution has been mainly concentrated throughout Mediterranean countries, Africa and part of Asia. In the past century, however, the date palm was introduced to North America, Australia and throughout Europe. Date production is currently a world agricultural industry, producing millions of metric tones of fruit a year, and marketed all over the world as a high-value confectionery and fruit crop. Moreover, the main ornamental tall palm planted in the gardens and the streets of many coastal cities are palm trees.

Despite its popularity amongst humans, diseases and pests plague the date palm tree. One such pest is the *Rhynchophorus ferrugineus*, or, the red palm weevil (RPW), also commonly known as the Indian palm weevil. The RPW was first observed in the Middle East region in the mid-1980's and have since been detected in trees in at least 19 countries around the world. As of the mid-1990's, approximately 5-6% of date palms in the Middle East were infested with the RPW, at an increasing annual rate of infestation (Food and Agriculture Organization of the United Nations, (FAO)). The cause of the high rate of spreading of the RPW is human intervention, by transporting infested young or adult date palm trees and offshoots from contaminated to uninfected areas. Currently, in all countries, it is illegal to transport a date palm tree in any form, even within the country itself. Moreover, in light of international laws, countries are required to report sightings of the RPW to the FAO.

Infestation is often not apparent until extensive damage has already been caused, and the tree is beyond recovery, resulting in the death of the tree. Infestation can be observed by wilted or yellow inner leaves and smelled by a characteristic rotting odor. Small round holes at the sites of removed offshoots and oozing out of a reddish brown fluid are also a clear indication of the presence of the RPW. Additionally, cocoon, weevil and pupal fibers are frequently found in the palm leaf base. The clearest sign of infestation is a tree that has fallen due to internal rotting.

Adult females lay several hundred eggs at the base of young leaves or in wounds to the leaves or trunk. Damage to date palms is caused mainly by the larvae, which hatch after 2-5 days. The hatched larvae burrow into the trunk and feed on the soft fibers and tissues of the stem. Just prior to pupating, they move towards the exterior of the tree, making tunnels and large cavities along the way. They can be found any place along the length of the tree. The larval period lasts from about 1-3 months when the larvae pupate inside fibrous cocoons and emerge as adults.

Generations of the RPW at all life stages can be present within a single palm tree. Typically, adult weevils present in a palm will not move to another one while they can still feed on it.

Measures that have been taken to prevent the spread of RPW have not been successful. The late detection of the presence of the RPW constitutes a serious problem in battling the pests. Despite various attempts, no safe techniques for early and consistent detection have been devised.

Nevertheless, there have been numerous measures devised for ridding trees of these pests. One common method of treatment comprises injecting chemical insecticides, including synthetic pesticides and botanicals, in either liquid or gas form, into the tree or individual insects. Anti-microbial products, which kill the micro-organisms that grow on the wood and in the stomach of the RPW may also be added. However, use of intensive chemical treatments (e.g. ConfidorR (Bayer)) has not been fully effective, and concerns have arisen over the environmental impact of the use of such chemicals. An alternative method is to cut down infested palms and destroy them before adults emerge from the tree. Prophylactic treatment of palms with insecticides is also an option, but the costs involved may be prohibitive. Mass trapping of RPW in buckets baited with cruentol and "pal esters" has high potential to reduce infestations.

One of the newest methods for monitoring and controlling RPW is bioacoustic methods, which measure sound emissions of the RPW at early stages of infestation. Sound emissions by the RPW can be detected and measured. Different sound emissions are classified into different groups for determining the lifecycle stage of the RPW, and the detection of the presence of the RPW is possible within only a few weeks of infestation of the tree.

Additionally, successful tests have been carried out in which dogs were used to locate infested trees. Insects feeding on plants produce a unique signature of chemical compounds, which can be smelled. Dogs are trained to recognize this smell and are sent to date palm plantations suspected of being infested with the RPW. (J. Nakash et al.; A Suggestion to Use Dogs for Detecting Red Palm Weevil (*rhynchophorus ferrugineus*) Infestation in Date Palms in Israel)

The infestation of the date palm tree by the RPW as described above is merely one example of an arthropod that causes destruction to an important tree species. Other arthropods that destroy the date palm tree include the Fruit Stalk Borer (*Oryctes elegans*) and the Stem Borer (*Jebuses Hammerschidti*). The Coconut Rhinoceros Beetle (*Oryctes rhinoceros*) is known to attack many species of palms including coconut, betel nut, sago palm and the dates. Many other significant species of trees throughout the world are vulnerable to infestation by various species of arthropods. One other example of an arthropod that damages trees is the moth (*Zeuzera pyrina* L.), which is known to cause serious damage to apple, pear and olive trees. The list of species of infested trees, as well as the list of species of infesting pests, is long, and methods of detection and treatment are generally chosen from at least one of those mentioned herein above, although other methods may be used as well.

U.S. Pat. No. 4,283,629 discloses a method and apparatus for detecting disease in a tree. U.S. Pat. No. 4,283,629 is particularly concerned with recognizing damage caused by red rot disease of a tree early in the infestation of a living tree. Red rot is caused by the fungus *Fomes Annosus*, which attacks mainly needle trees, such as spruce and pine, as well as the larch, Douglas fir and others. The fungus mainly grows in standing (live) trees, and moves upwardly from the bottom of the trunk. It causes a root rot, which, in the pine ultimately leads to the death of the tree, and in the spruce destroys the wood inside the trunk, but does not threaten its life. U.S. Pat. No. 4,283,629 utilizes computer tomography for measuring the coefficient of absorption of the trunk of the tree for gamma and/or neutron radiation. A change in the coefficient due to rot or other factors is detected. U.S. Pat. No. 4,283,629 does not attempt to identify the pest infesting the tree, but rather the cavities in the tree formed by the pest. A supporting frame surrounds and is preferably fastened to the trunk, a beam of radiation is passed through the tree at various positions from a radiation source to a detector and the coefficient of absorption at each position is converted into a computerized topographic display. U.S. Pat. No. 4,283,629 does not describe the means by which the apparatus is lifted and secured to the tree, although this does not appear to be a simple or standard procedure. Moreover, when desiring to use the apparatus of U.S. Pat. No. 4,283,629 on many trees, the dismounting and remounting procedure will take a lot of time, and will likely add to the costs involved.

It is an object of the present invention to provide a method and system for detecting the presence of pests in a body.

In one embodiment it is desirable to provide a method and system for the detection of the presence of pests in a body, which utilizes a portable (or, mobile) apparatus.

In one embodiment it is desirable to provide a method for the detection of pest infestation of a body, which utilizes an apparatus that is capable of being shifted along a predetermined length.

In one embodiment it is desirable to provide a method for the detection of the presence of pests in a body, which utilizes an apparatus that does not make physical contact with the tree during the detection process.

Additional advantages of the present invention will become apparent as the description proceeds.

SUMMARY OF THE INVENTION

The present invention relates to a method for detecting pest infestation within a body, said method comprising the steps of:
a) providing an imaging system comprising at least a radiation source, a detector, a processing station and a display monitor;
b) positioning at least a section of said body between said radiation source and said detector;
c) acquiring a first image of said section of said body;
d) acquiring at least one second image of said section of said body;
e) removing the common portion of said images by subtracting said first image from said second image, thereby resulting in a subtracted image; and,
f) determining from said subtracted image whether at least one pest is present within said body.

The present invention further relates to an imaging system for detecting pest infestation within a body, said system comprising:
a) a mobile imaging apparatus defining an optical axis; and a positioning system for positioning the imaging apparatus along a length of a body transverse to the optical axis;
b) a processing station; and
c) a display monitor;
wherein the processing station is arranged to perform the steps of:
a) acquiring a first image of at least a section of said body;
b) acquiring at least one second image of said section of said body; and
c) removing the common portion of said images by subtracting said first image from said second image, thereby resulting in a digitally subtracted image.

DETAILED DESCRIPTION

The infestation of various objects or bodies by pests is widespread in many countries throughout the world. The damage that pests cause can have detrimental affects on international industries as well as on the local environment. The present invention provides a solution to this problem by providing a method and system for determining a presence of pests at all stages of infestation in all forms of bodies. The system is portable and may be transferred from one body to another to allow a plurality of bodies to be 'scanned' in a relatively short amount of time.

An illustrative, but non-limitative, example of the present invention is a method and system for determining whether a tree is infested with pests, and for killing the pests in situ. Although the present invention is described herein with reference to a tree trunk, it is important to emphasize that the present invention is useful for detecting living subjects visually confined within any body, in particular, within all forms of vegetation and at all stages in the life cycle, including both living and felled tree trunks, logs and branches, as well as offshoots, plants and roots. By visually confined is meant that the subjects are not visible by visible or near visible light. Other bodies which may be detected with the present invention for pest infestation include cotton fiber and food items such as fruits and vegetables. Additionally, the present invention may be utilized for detecting pest infestation in enclosed containers (or, bodies) such as bags, barrels, boxes, etc. within which are contained any object as mentioned above, as well as all varieties of grains and seeds. Furthermore, the method and system can be used for examining the integrity of wood constructions, e.g. within buildings. In some of the above mentioned items, particularly with reference to food items, detection of pest infestation is primarily utilized for allowing the user to remove and/or discard the food items containing the pests, and not for killing the pests.

It is also understood that the system of the present invention as described herein must be transported to and positioned around a living tree, whereas felled trees, offshoots, etc. may be transported to the system. This distinction will likely affect the costs involved in performing the detection procedure.

The term, "pest" as used herein refers to any organism that infests and causes damage, in particular, to a plants, vegetables or trees, particularly arthropods such as wood-boring insects, including moths, beetles, nematodes, etc. More particularly, such creatures include: Asian Long-horned Beetle, Bronze Birch Borer, Dogwood Borer, Elm Bark Beetle, Giant Palm Weevil, Bark Beetle, Metallic Wood-boring Beetle, Clear-winged Moth, Carpenter Moth, Horntail Wasp, Leafcutter Bee, Carpenter Ant, Red-headed ash borer, Cottonwood borer, Locust borer, Twig girder. Typically, the pest is in the form of a grub or larva, but it is desirable to detect the pest at any stage in its life cycle for the purpose of killing it. Thus, the present invention is concerned with pests in egg form, as larvae, as pupae and as arthropods. Killing the pests prevents damage or further damage to the tree it currently lives in as well as prevents future damage to a different tree that it may fly to and infect. Unless otherwise specified, these terms are used essentially interchangeably herein. In the present invention, the term, "Red Palm Weevil" (RPW) refers to a specific example of one such organism. However, the term, "pest" is understood to also include any organism that infests and causes damage to any of the bodies as mentioned above. The term, "infestation" as used herein refers to the presence of at least one, but typically a plurality of pests present within a body.

Figure 1:
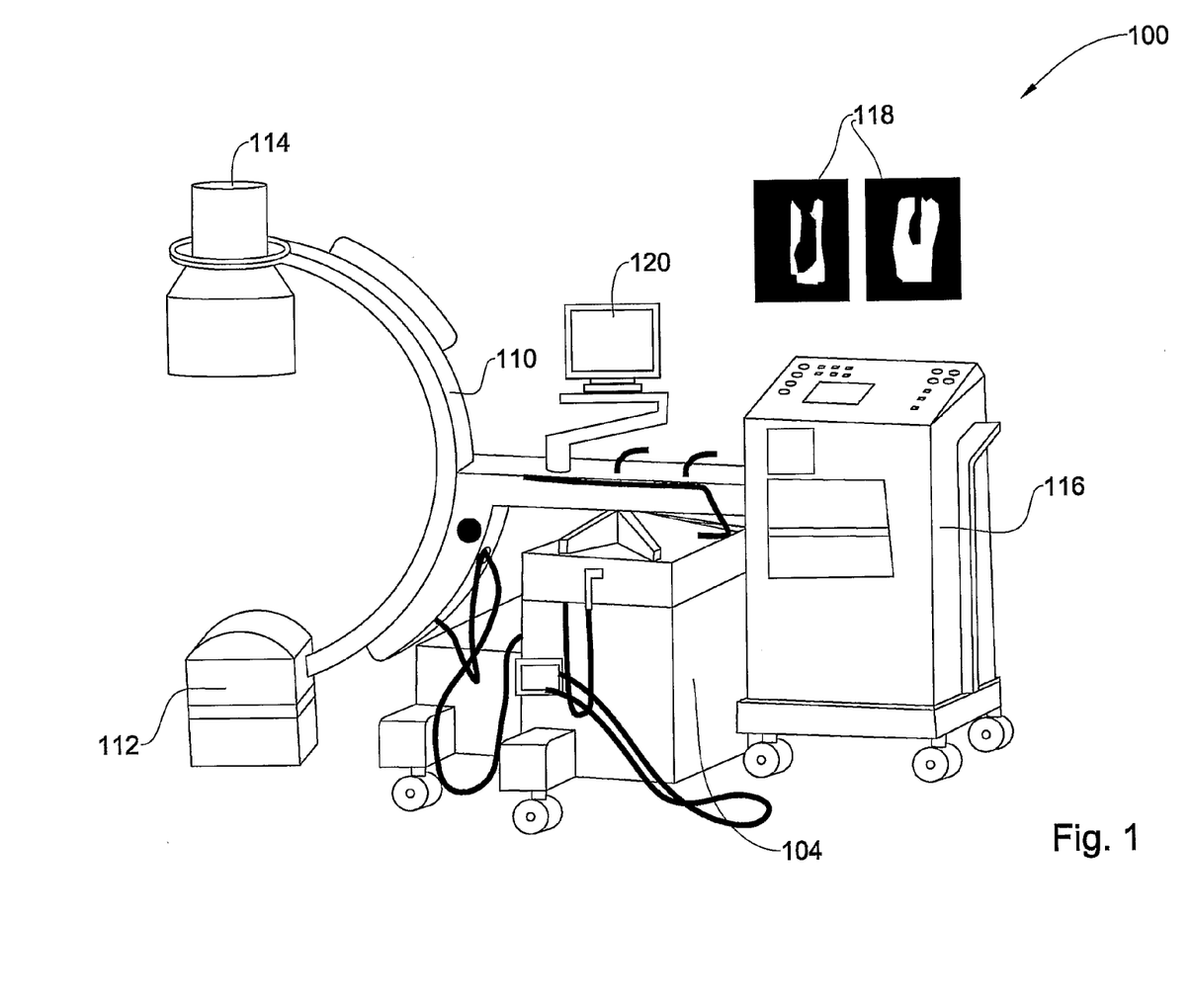
FIG. 1 illustrates the system utilized in the present invention for detecting pest infestation of trees.

FIG. 1 shows an embodiment according to the present invention, comprising an imaging system (100), shown in this embodiment as essentially a conventional C-arm shaped x-ray system, comprising generally a control center display (120) and a mobile stand (104) for supporting and positioning the C-arm apparatus (110) around a tree or a portion of a tree as described herein. C-arm apparatus (110) comprises a radiation source (112) situated opposite a radiation detector (114). Detector (114) comprises an image intensifier and a digital video camera. A processing station (116) comprises digital image processing software and two display monitors (118) for use during a digital subtraction angiography procedure, as described herein below. In particular, the processing station is arranged to execute the steps of acquiring a first image of at least a section of said body; acquiring at least one second image of said section of said body; removing the common portion of said images by subtracting said first image from said second image, thereby resulting in a digitally subtracted image.

Figure 2:
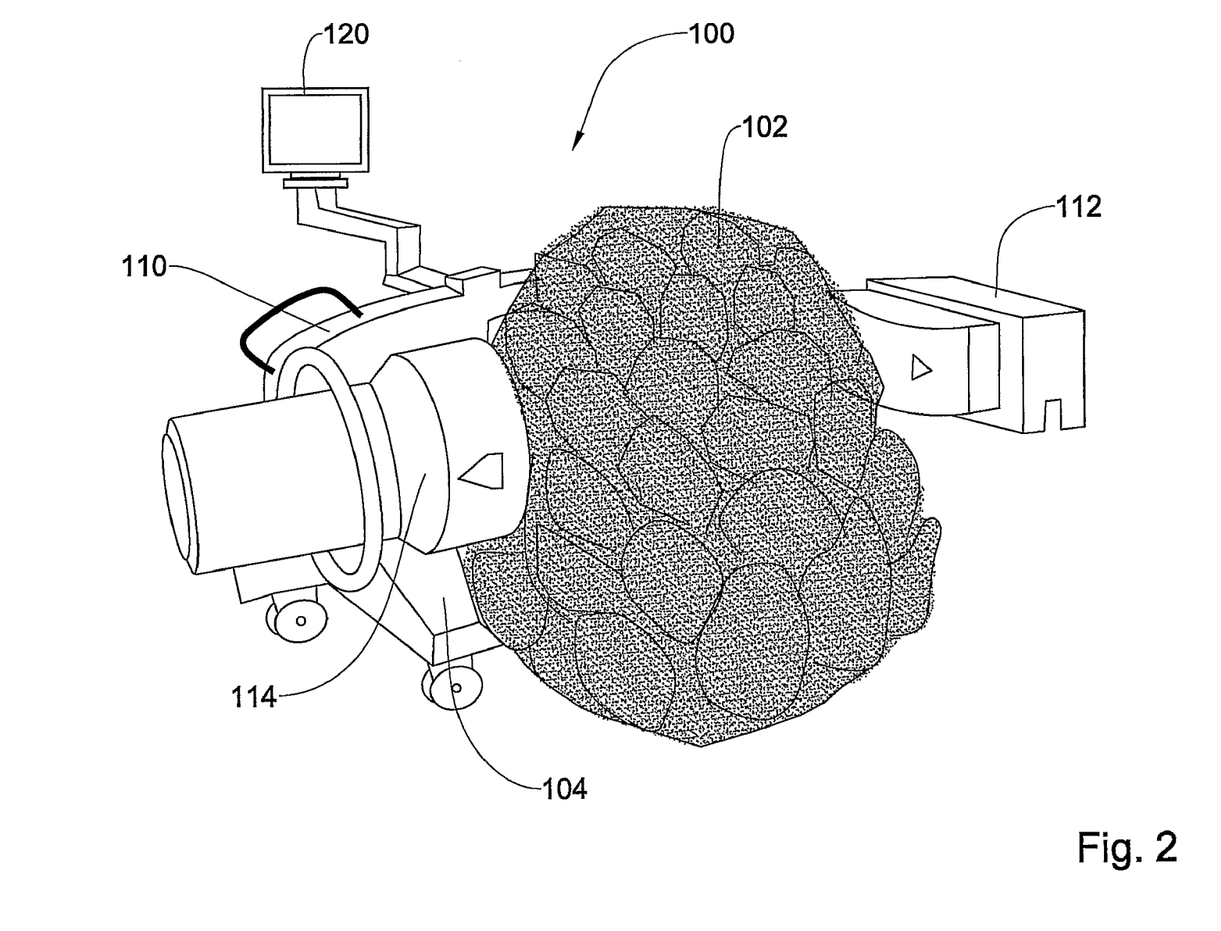
FIG. 2 illustrates a preferred embodiment of the present invention wherein the base of the trunk of a date palm tree is inspected for infestation.

FIG. 2 shows a portion of the trunk of a date palm tree (102) disposed upright between radiation source (112) and detector (114) of C-shaped arm (110).

The C-shaped arm x-ray system shown in FIG. 2 may be an imaging system that is traditionally used in medical applications, and particularly in minimally invasive surgeries by reducing pain and trauma to the patient and decreasing costs involved. One type of C-shaped arm that can be used in the present invention, is the Ziehm Vision C-arm manufactured by Ziehm Imaging, Inc., although any C-arm comprising the desired components and features, as described herein, may be used. It is understood that the C-arm may also be modified according to the different embodiments and aspects of the invention as described herein below. Alternatively, a flat detector (not shown) may be used instead of detector (114), thereby eliminating the need for an image intensifier and video camera. Alternatively, other imaging systems and technologies that comprise the desired components and features may be used, including CT, MRI and PET systems, as well as other shaped arms, such as a U-shaped arm.

The imaging system (100) may comprise software, similar to software used for acquiring digital radiographs via digital subtraction angiography (DSA). DSA is an electronic technique used on humans to visualize blood vessels with contrast medium in a bony environment by subtracting the pre-contrast image (the mask) from the image with the contrast medium. The present invention utilizes digital subtraction in order to identify moving pests within the tree (102).

The conventional technique of DSA involves first acquiring a radiograph image at a predetermined location of the body of the patient, then injecting a contrast medium at the said location, and acquiring a second image after the contrast medium reaches the blood at the said location. When the mask image is subtracted from the image with the contrast medium the static tissue and bone of the body that is common to both images is removed and the blood flow of the patient may be observed clearly in the new subtracted image.

In contrast to conventional DSA, in a preferred embodiment of the present invention, digital subtraction of images is employed without the use of a contrast medium (which is known herein as Digital Subtraction Imaging, or, DSA). In particular, according to an embodiment, contrast fluid may be injected only after acquiring a digitally subtracted image, in particular, by injecting contrast fluid near the detected pests. It is noted that unlike the human body, the plant bodies generally cannot receive contrast fluids without damage, reason why this can only be administered after identifying the pest. According to the present invention, it is desirable to detect the movement of the larva inside the tree in order to confirm their existence and then pinpoint their position to later kill them. According to the present invention, a section of the tree is positioned between the radiator source and the detector, and a first, or mask image of the tree is obtained.

In addition to acquiring a single second image, a plurality of second, or, evaluation images may be then obtained of the same section of the tree as the mask image. The mask image is eliminated from the evaluation images by subtracting the static structure of the tree that is common to both images, such that the moving larvae present within the tree are clearly visible in the new subtracted image even though they where not visible, or barely visible before the subtraction. The evaluation images may be acquired at a fast rate, for instance, 25-30 images per second. After image subtraction is performed, the plurality of evaluation images are played back in rapid succession to represent the movement of the larvae.

It is understood that although the mask image is referred to herein as the 'first' image, and the evaluation images as the 'second' images, the order by which the images are acquired (i.e. whether the mask image is acquired first or last) is not crucial to the present invention.

Figure 3:
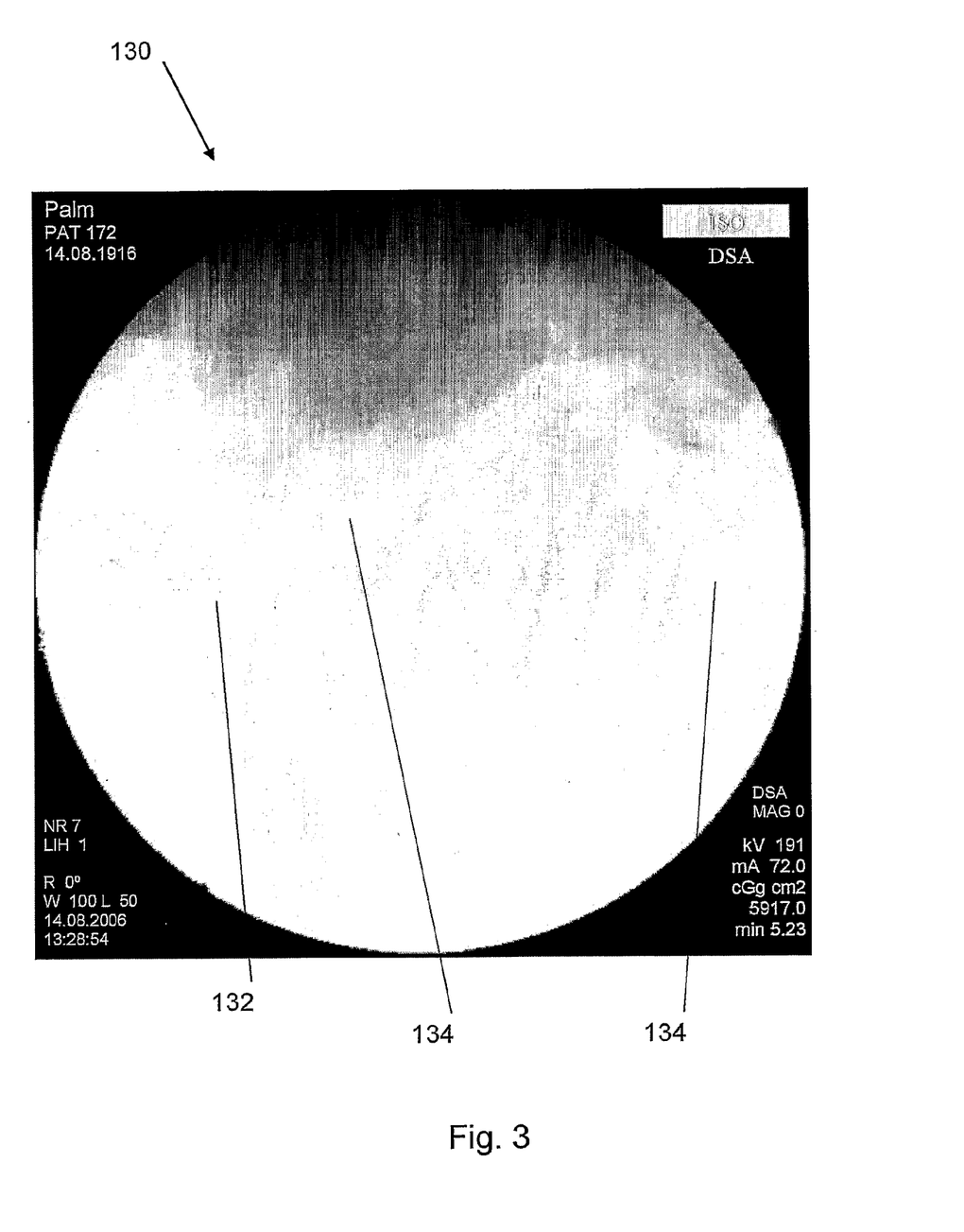
FIG. 3 illustrates a first image of a section of the tree trunk of FIG. 2, showing a tunnel and larva unclearly.
Figure 4:
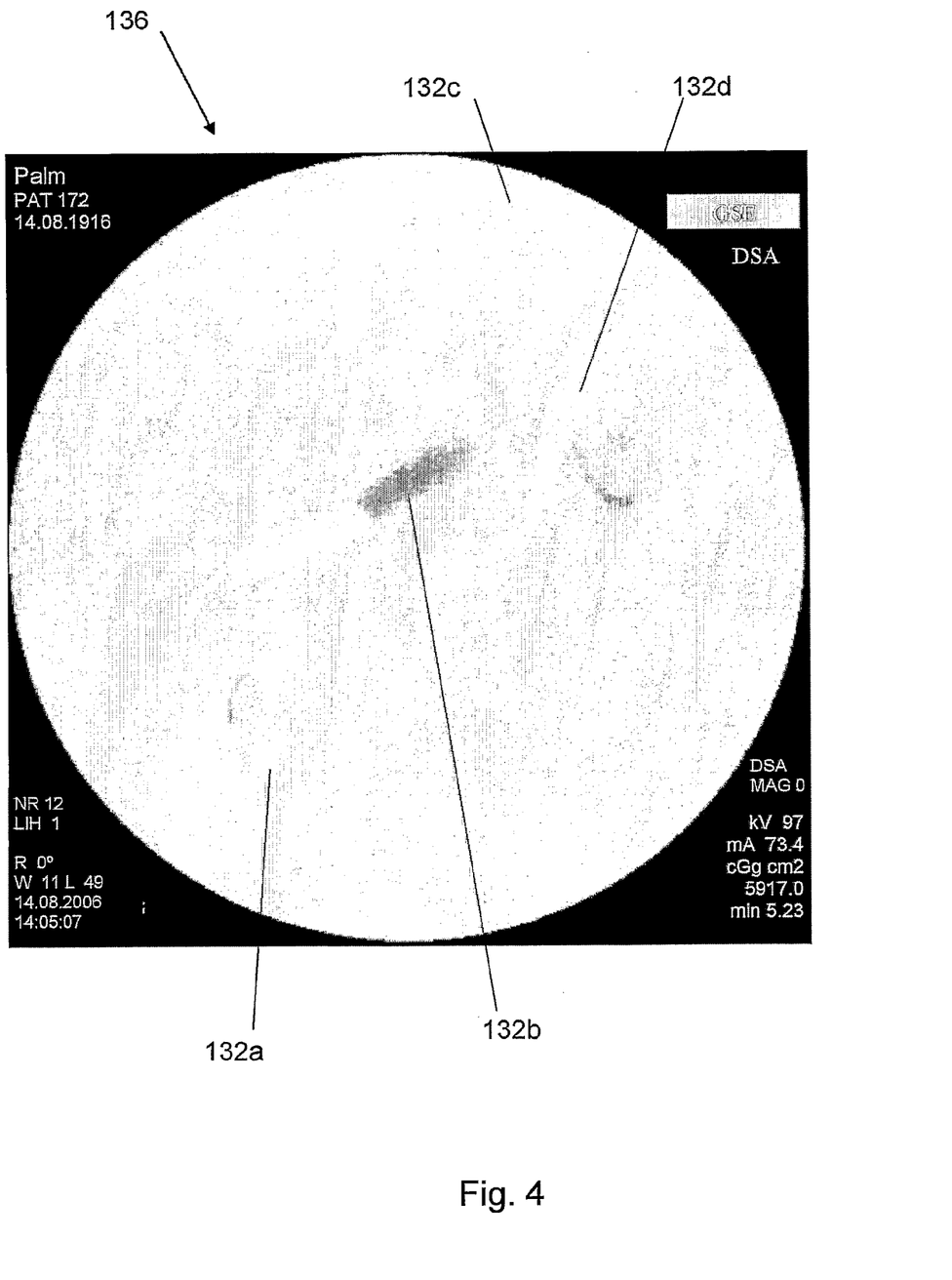
FIG. 4 illustrates a second image of a section of the tree of FIG. 2, after performing image subtraction, clearly showing a plurality of larvae.

Referring to FIG. 3, a first image or mask image of a tree is shown indicated by numeral (130). Even after close inspection in mask image (130) a larva (132) and a tunnel (134) may be barely made out as a fuzzy outline. However, after digital subtraction is performed, at least four larvae (132a)-(132d) may be clearly seen throughout the subtracted image (136), as shown in FIG. 4. Thus, while it may be possible to determine that there is infestation of the tree by viewing the mask image (130) alone, there is undeniable indication of infestation when viewing the second image (136). It is understood that only a single second, or evaluation image is required to perform image subtraction since the location of the larva in the mask image will not be the same location of the larva in the second image.

However, by obtaining a plurality of evaluation images, the movement of the larva may be better observed, as described herein above.

C-arm shaped x-ray imaging systems as well as image subtraction are well known to the man skilled in the art, therefore a technical description of the same is not necessary. The image subtraction of the present invention may utilize any appropriate algorithm, including linear subtraction and logarithmic subtraction.

After locating the larva (or, larvae) and one or more tunnels, it may be desirable to inject a contrast medium, or dye, through the tree into the tunnels. The contrast medium may be ionic or non-ionic. The contrast medium flows through the tunnels, either upward or downward, depending on the location from which the larvae traveled. Additional evaluation images are then acquired and digital subtraction is performed. Injecting (or, flooding) the tree with the dye allows the user to determine the size of the hole or tunnel within the tree, which enables the damage to be evaluated. Additionally, during the killing stage (as described herein below) the presence of the dye can indicate to which area within the tree the killing agent was applied. Moreover, the user may be able to reveal additional larvae or eggs along the length of the tree, which may be later killed.

After detecting at least one larva in a tree, and determining that the tree is infested, it is desirable to kill the larva as soon as possible, preferably, in situ. To that end, the position of the larva must be identified in order to inject it with a pest-killing agent. Injection of a pest-killing agent is performed according to conventional means, and using a conventional device.

Other possible methods of killing the pest, not described above, include puncturing individual larvae with a drill or needle and/or sucking the larvae empty with a drill or needle; introducing hot steam, smoke or laser to the inside of the tree; electrocution, preferably after first flooding the tree with a liquid; irradiation of the tree; and insertion of insect pathogenic nematodes, fungi, bacteria and/or viruses to the tree.

Figure 5:
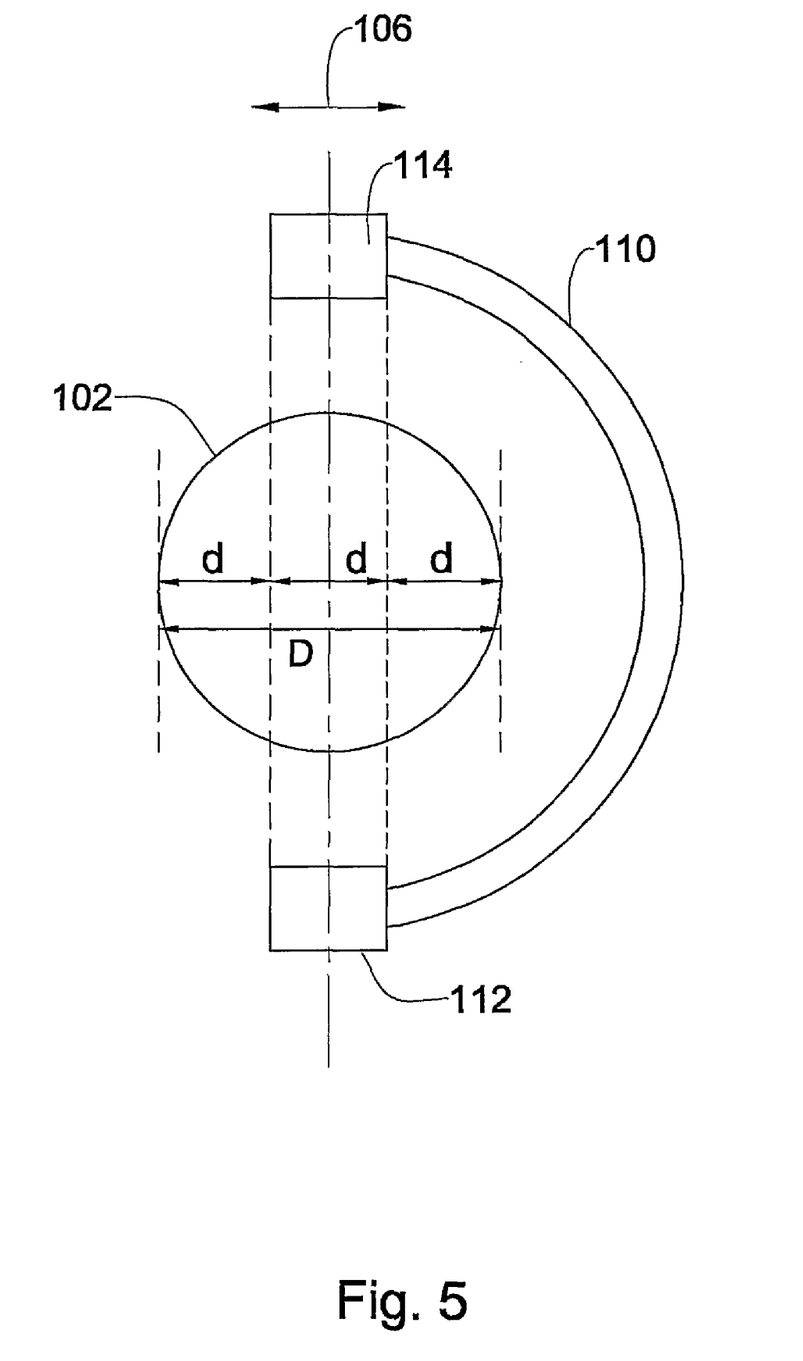
FIG. 5 illustrates a schematic top view of FIG. 2.
Figure 6:
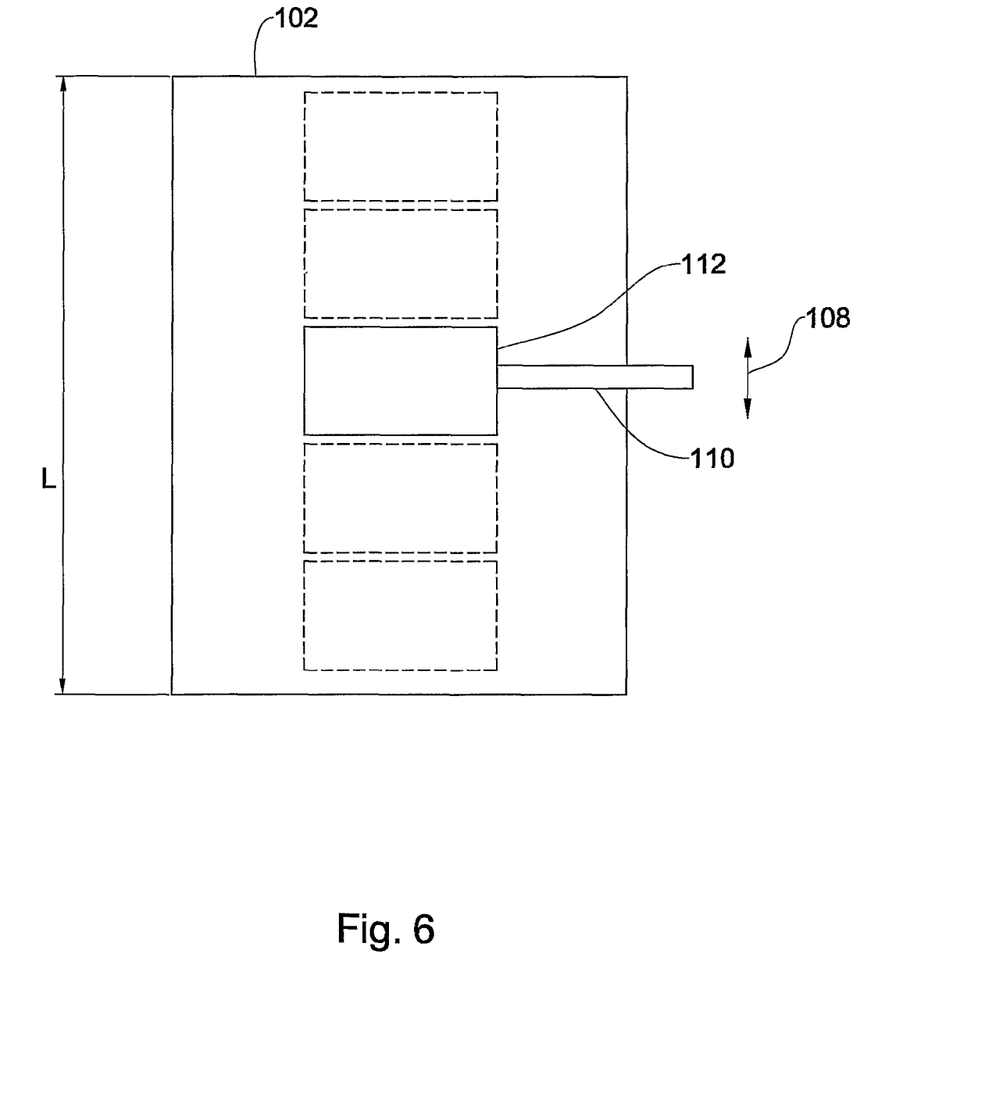
FIG. 6 illustrates a schematic side view of FIG. 2.

Referring to FIG. 5, a schematic top view of FIG. 2 is shown, wherein tree (102) comprises, for illustrative purposes only, a maximum width, or diameter (D) of 90 cm, thereby divided into three 30 cm segments. Hence, again for illustrative purposes only, when imaging system (100) has a field of view of 30 cm×30 cm, in order to be able to view the entire cross-section of tree (102), C-arm apparatus (110) must be shifted as indicated by arrow (106) such that at least three images are acquired, each having a width (d) of 30 cm. Similarly, as indicated in FIG. 6, showing a schematic side view of FIG. 2, multiple images must be acquired by shifting C-arm apparatus (110) along the length (L) of tree (102), as schematically indicated by positioning system (108), in order to view the entire length (L) of tree (102). The positioning system 108 is preferably arranged to locate the object's central axis and to position the x-ray apparatus to image only a section along the central axis of said body and may for example comprise a lift for lifting the x-ray apparatus, typically over a length between 2 and 20 meter.

It is understood that the lengths and measurements mentioned herein are used merely as examples and should not be construed as limiting the scope of the invention. The present invention may be used to scan and acquire images at all locations along all portions of trees including the trunk, branches, offshoots and plants of all shapes and sizes, wherein the size and shape of the imaging system is adjusted or predetermined accordingly.

Figure 7A:
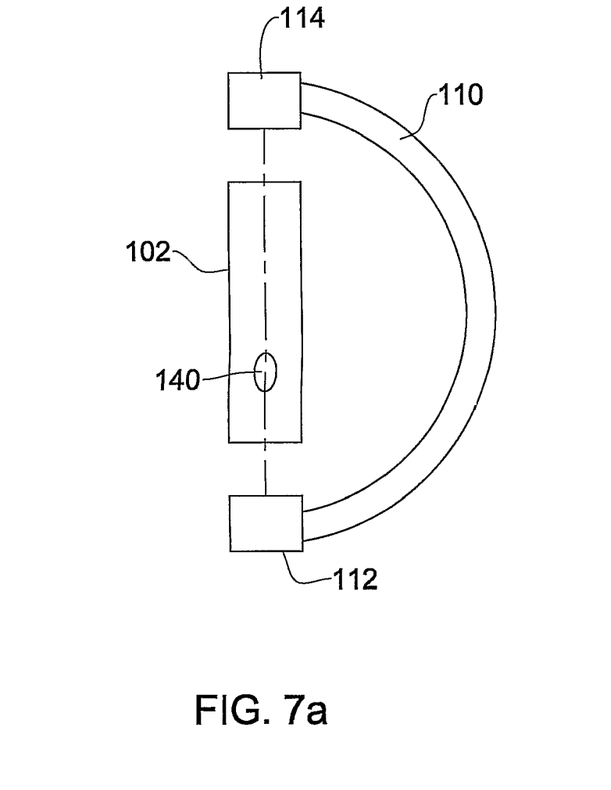
FIGS. 7A-7C illustrate schematically the method of determining the exact position of a larva within a tree.
Figure 7B:
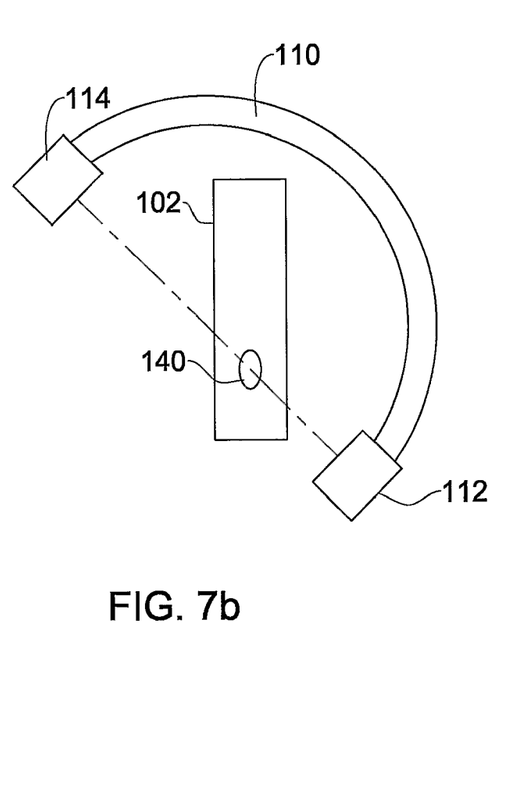
Figure 7C:
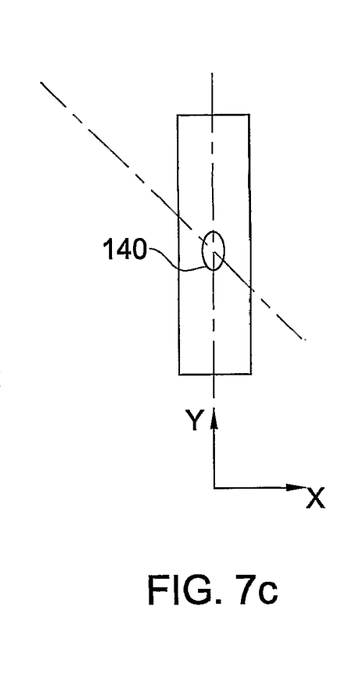

According to the present invention, for each 30 cm×30 cm area, a mask image is acquired, then a plurality of evaluation images are acquired, until images of the entire tree, or a desired portion thereof are acquired. FIG. 7a shows schematically a top view of a portion of tree (102) disposed between radiation source (112) and radiation detector (114), wherein a larva (140) is situated. In this position a first image is acquired. Note that for clarity, only the section of tree (102) disposed between the radiation source (112) and detector (114) is shown. The presence of larva (140) within the field of view of the detector is observed. Next, C-shaped arm arm apparatus (110) is rotated after rotating the imaging system over an angle around an axis transverse to an optical axis of the imaging system, for acquiring a shifted second image; and determining the subject's depth position as a function of subject shift and rotation angle over a predetermined angle around an axis of rotation transverse to the optical axis of the imaging system as shown in FIG. 7b, and a second shifted image is acquired from the new angle. The position of larva (140) within the field of view of the detector at the new angle may then be determined at the intersection point of the two, as a function of the larva's shifted position and rotation angle, as shown in FIG. 7c. Once the exact position of larva (140) within tree (102) is determined, the pest is killed by injecting a pest-killing agent, such as a chemical, bacteria, etc. as described herein above, to larva (140).

It is important to mention that although the larva is in motion within the tree, the change in position that occurs between the time the images area acquired and the larva is detected, to the time of the injecting of a killing agent, is negligible.

It is generally desirable to begin acquiring images at the center of the tree. This is because the likelihood of larvae to be situated at the center of the tree is often greater than at its periphery, since the wood at the central core of the trunk, known as heartwood, is generally softer, and therefore easier to bore tunnels through, than that at the periphery of the trunk. There are several alternative methods that may be utilized to determine the location of the central axis of the tree. One method comprises measuring, for instance, via laser, the distance between the radiation source and the tree, and between the detector and the tree, and subtracting these measurements from the known axial distance between the source and the detector. The result calculated from this equation is the width of a section of the tree at a particular location along the tree. These measurements are repeated along the entire cross-section of the tree. The largest result for the width of the tree will typically be at the central axis of the tree, or close thereto. Determining the distance between the source and detector, and the tree, is also useful in determining the angle by which the C-arm should be rotated, as described herein above. For instance, if the distances are large, i.e. the width of the tree at the location of the measurement is narrow, a larger angle of rotation may be required than when the width of the tree is wider.

Moreover, prior to injecting the pest killing agent, as described herein above, the above measuring method may be used to determine the closest location along the periphery of the tree to the larva or tunnel from which the agent should be injected.

Alternatively, the location of the central axis of the tree may be determined by radiating the tree along its cross-section. When there is less material (i.e. the tree is thinner) between the source and the detector, more energy will pass than when there is more material there between. Thus, the location where the least amount of radiation is detected is most likely at the central axis of the tree.

A further alternative method of determining the location of the central axis of the tree comprises recording the width of the tree, for instance via a video camera, and displaying the recording on a monitor on which a grid is situated. The center of the tree may be observed by determining the grid square at the center of the grid squares within which the tree is situated.

Alternatively, other methods that are not described herein may be used to determine the central axis of the tree. Nevertheless, it is only preferred to concentrate on the center of the tree, but by no means a requirement of the present invention.

The above-described methods of measurement may be also used to precisely measure the length (and/or width) of the pest itself as well as that of the tree. Moreover, measurements of the tree may be determined from the image of the tree obtained by the imaging system.

As described herein above, the present invention is useful for detecting pests present within trees of all forms and at all stages in the life cycle, including both living and felled tree trunks, logs and branches, as well as offshoots and plants. As mentioned above as well, for a living tree the system of the present invention must be transported thereto. Various governmental authorities in different countries or regions require scanning at different locations along the length of a tree in order to declare the tree free of pests and approve the tree for transportation. For example, currently, the government of Spain requires the scanning of the top third of the tree, whereas the government of Israel requires the scanning of the bottom third of the tree.

In one embodiment, a positioning system for vertically lifting x-ray apparatus (110) along the length of a living tree trunk is provided. In particular, preferably, the positioning system is arranged to position the x-ray apparatus along a length of the body transverse to the optical axis defined by source 112 and detector 114 of the x-ray apparatus 110. Lifting may be accomplished by any known mechanical means such as a fork lift or any form of telescopic lifter, powered by means such as pneumatic, hydraulic, etc. Preferably, the x-ray apparatus (110) may be lifted up to 20 meters, although lifting to higher elevations may be desirable in some cases. The connection between the liftable x-ray apparatus (110) and the image-processing unit may be via an elongated cable or wireless technology, such as Bluetooth™.

According to one embodiment of the present invention, a system for detecting pests along the length of the trunk of a vertically oriented tree includes a first, or, immobile C-arm apparatus, which is fixedly joined to the image processing unit, and a second, or, mobile C-arm apparatus which may be lifted along the vertical length of the tree, and which is in communication with the processing unit as described above. The immobile C-arm apparatus is provided for performing the pest detection along a predetermined, limited length of the trunk, typically close to the base. The mobile C-arm apparatus is provided for performing the pest detection along a length of the trunk greater than that allowed by the immobile C-arm apparatus.

It is understood that when the tree is felled the trunk may be oriented in a horizontal plane relative to the floor, and the C-arm apparatus is shifted accordingly, mutatis mutandis.

Both in the laboratory and in the field, users of the system of the present invention should be suitably protected from overexposure to radiation by wearing appropriate gear and positioning themselves out of the way of the radiation.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims. In essence, the invention utilizes the notion that the living subjects to be show their presence, due to their movements, in the subtracted images. This notion can be utilized using other type of imaging systems such as acoustic imaging systems without departing from the scope of invention.

The invention claimed is:

1. A method for detecting pest infestation within a body, said method comprising the steps of:
    a) providing an imaging system comprising at least a radiation source, a detector, a processing station, and a display monitor;
    b) positioning at least a section of said body between said radiation source and said detector;
    c) acquiring a first image of said section of said body;
    d) sequentially acquiring at least one second image of said section of said body to visualize the movement of a pest subject;
    e) removing the common portion of said images by subtracting said first image from said second image, thereby resulting in a subtracted image; and,
    f) determining from said subtracted image whether at least one pest is present within said body.

2. The method according to claim 1, wherein the second image is acquired time-shifted from the first image.

3. The method according to claim 1, wherein the second image is acquired after rotating the imaging system over an angle around an axis transverse to an optical axis of the imaging system, whereby acquiring a shifted second image; and determining the subject's depth position as a function of subject shift and rotation angle.

4. The method according to claim 1, wherein a plurality of second images are sequentially acquired to visualize the movement of the subject.

5. The method according to claim 1, wherein a contrast medium is introduced to the body after acquiring the second image.

6. The method according to claim 1, wherein the body may be chosen from any one of the group consisting of:
    a) vegetation;
    b) food;
    c) enclosed containers; and
    d) wood construction.

7. The method according to claim 1, wherein the body is a tree trunk that is positioned between the radiation source and detector for only imaging a section along the central axis of said body.

8. The method according to claim 6, further comprising determining the pest's position and injecting a pest treatment agent to said body at the detected pest position.

9. An imaging system for detecting pest infestation within a body, said system comprising:
    a) a mobile imaging apparatus defining an optical axis; and a positioning system for positioning the imaging apparatus along a length of a body transverse to the optical axis;
    b) a processing station; and
    c) a display monitor; wherein the processing station is arranged to perform the steps of:
        a) acquiring a first image of at least a section of said body;

b) sequentially acquiring at least one second image of said section of said body to visualize the movement of a pest subject; and c) removing the common portion of said images by subtracting said first image from said second image, thereby resulting in a digitally subtracted image.

10. The imaging system according to claim 9, wherein the positioning system is arranged for rotation of the imaging system over an angle around an axis transverse to an optical axis.

11. The imaging system according to claim 9, wherein the imaging system comprises an x-ray radiation source and a detector, mounted to face each other on opposite sides of a C-shaped arm.

12. The imaging system according to claim 9, further comprising an immobile imaging apparatus for performing detection along a limited length of a body; and wherein the positioning system is arranged to move the mobile imaging apparatus along a length greater than said limited length.

13. The imaging system according to claim 9, wherein the positioning system is arranged to locate the body central axis and to position the imaging apparatus to image only a section along the central axis of said body.

14. The imaging system according to claim 9, wherein the positioning system comprises a lift for lifting the imaging apparatus over a length between 2 and 20 meter.

15. The method of claim 1, wherein said step d) comprises sequentially acquiring up to between 25 and 30 images per seconds.

* * * * *